US007569398B2

(12) United States Patent
Puget et al.

(10) Patent No.: US 7,569,398 B2
(45) Date of Patent: Aug. 4, 2009

(54) METHODS AND DEVICES FOR TRANSPORTING AND CONCENTRATING AN ANALYTE PRESENT IN A SAMPLE

(75) Inventors: Pierre Puget, Saint Ismier (FR); Patrick Pouteau, Voreppe (FR); Frédéric Ginot, St Egreve (FR); Patrice Caillat, Echirolles (FR)

(73) Assignee: Commissariat a l'Energie Atomique, Paris (FR)

( * ) Notice: Subject to any disclaimer, the term of this patent is extended or adjusted under 35 U.S.C. 154(b) by 631 days.

(21) Appl. No.: 10/416,207

(22) PCT Filed: Nov. 27, 2001

(86) PCT No.: PCT/FR01/03743

§ 371 (c)(1),
(2), (4) Date: May 8, 2003

(87) PCT Pub. No.: WO02/43865

PCT Pub. Date: Jun. 6, 2002

(65) Prior Publication Data

US 2004/0023273 A1 Feb. 5, 2004

(30) Foreign Application Priority Data

Nov. 29, 2000 (FR) .................................. 00 15417

(51) Int. Cl.
*G01N 33/543* (2006.01)
*G01N 33/553* (2006.01)

(52) U.S. Cl. ....................... 436/518; 436/523; 436/524; 436/526; 436/534; 436/541; 436/540

(58) Field of Classification Search ................. 436/518, 436/523, 524, 526, 534, 541, 540
See application file for complete search history.

(56) References Cited

U.S. PATENT DOCUMENTS

| | | | | |
|---|---|---|---|---|
| 5,498,392 | A | 3/1996 | Wilding et al. | |
| 5,603,760 | A * | 2/1997 | Berke et al. | 106/802 |
| 5,863,502 | A | 1/1999 | Southgate et al. | |
| 6,074,827 | A | 6/2000 | Nelson et al. | |
| 6,342,396 | B1 * | 1/2002 | Perrin et al. | 436/518 |

FOREIGN PATENT DOCUMENTS

| | | | |
|---|---|---|---|
| WO | 94/26414 | A1 | 11/1994 |
| WO | 98/10267 | A1 | 3/1998 |
| WO | 00/50172 | A1 | 8/2000 |

* cited by examiner

*Primary Examiner*—Mark L Shibuya
*Assistant Examiner*—Pensee T Do
(74) *Attorney, Agent, or Firm*—McKenna Long Aldridge LLP

(57) ABSTRACT

The present invention relates to a method of transporting an analyte present in a sample, to a method of concentrating an analyte present in a sample, and to a device for implementing these methods. In the method of transporting an analyte present in a sample of the present invention, a solution A in which the analyte is attached to magnetic particles is prepared from the sample; the solution A is introduced into a first container connected via a bottleneck to a second container; and the analyte attached to the magnetic particles is moved, by means of a magnetic system, from the first container to the second container via the bottleneck, the second container being filled with all or part of the solution A and/or with another solution.

10 Claims, 2 Drawing Sheets

METHODS AND DEVICES FOR TRANSPORTING AND CONCENTRATING AN ANALYTE PRESENT IN A SAMPLE

TECHNICAL FIELD

The present invention relates to a method of transporting an analyte present in a sample, to a method of concentrating an analyte present in a sample, and to a device for implementing these methods.

It falls within all fields in which there is a need to transport an analyte from a first solution to a second solution, for example for reasons of incompatibility of the solution consisting of the sample, or of elements present in this solution, with a reagent or a chemical process targeting the analyte.

It also falls within all fields in which there is a need to concentrate an analyte in order to be able to demonstrate it, for example by reacting it with a reagent for converting and/or demonstrating the analyte for example.

Many in vitro diagnostic tests consist, for example, in chemically reacting an analyte being sought with a suitable reagent. The, or one of the, products of the reaction is then detected directly or indirectly.

Mention may, for example, be made of immunoassays in which the chemical reaction is an antibody/antigen recognition or, more generally, a protein/ligand reaction, and tests with nucleic acid probes in which hybridization between nucleic acids is detected.

A diagnostic test is all the better if it has both high sensitivity and high specificity. It is all the more sensitive if it makes it possible to detect a small amount of analyte being sought. It is all the more specific if it is positive only for the analyte being sought and not for similar analytes.

The term "analyte" is intended to mean all or part of a corpuscle or molecule intended to be isolated, to have its medium changed and/or to be concentrated in order to be used and/or demonstrated, such as a microorganism, a bacterium, a fungus, a virus, a eukaryotic cell; a chemical compound; a molecule such as a peptide, a protein, an enzyme, a polysaccharide, a lipid, a lipoprotein, a lipopolysaccharide, a nucleic acid, a hormone, an antigen, an antibody, a growth factor, a haptene; a cell such as a tumour cell, etc.

STATE OF THE ART

Many diagnostic tests are carried out after steps of extracting the target analytes from biological samples, of purifying in order to remove parasitic products which penalize the performance of the test, of concentrating the target analytes in order to increase the amount of analyte per unit of buffer volume, and of dissolving the target analytes in a buffer in order to make them chemically accessible.

In addition, in order to increase the sensitivity and the specificity of a test for demonstrating an analyte, it is sometimes necessary to reduce the volume of the buffer in which the copies of the analyte being sought are found, while at the same time conserving said analyte in its entirety.

Biologists have entirely conventional means for concentrating an analyte, in particular using centrifugation, filtration and/or magnetic sedimentation techniques. These techniques require transfers of solutions and manipulations of the analyte which lead to an inevitable decrease in the amount of analyte which can be analysed.

For example, in centrifugation and magnetic sedimentation methods, the actual centrifugation or magnetic sedimentation steps may have to be repeated several times, the limit of the number of repetitions being set by the minimum volume of solution which can be easily and reliably handled with a conventional pipette. This minimum volume is of the order of about 10 microliters. Below this, liquid, and therefore analyte, is lost by transporting it in "large" containers such as pipettes, flasks, etc. In addition, there are problems of evaporation and of adsorption to the walls of the containers during these manipulations.

In the case of a low concentration of analyte in the starting sample, this may cause the complete disappearance of the analyte or a decrease in the amount thereof such that it may become undetectable.

Besides the abovementioned drawbacks, these manipulations are expensive in terms of material and take a lot of time.

This remains a constant problem for many industrial applications, for example the detection of pathogenic microorganisms in a biological specimen or an industrial sample.

A real need therefore exists for a method and a device for transferring an analyte from a first solution to a second solution and/or concentrating an analyte while at the same time conserving the amount of analyte present at the start, for example in order to increase the sensitivity and the specificity of diagnostic tests and of any chemical reaction directed towards the analyte, and to overcome the abovementioned drawbacks.

The present invention satisfies this need, and has not only the advantage of overcoming the abovementioned drawbacks, but also many other advantages which those skilled in the art will not fail to note.

EXPLANATION OF THE INVENTION

The present invention provides a method of transporting an analyte present in a sample, in which:

- a solution A in which the analyte is attached to magnetic particles is prepared from the sample,
- the solution A is introduced into a first container connected via a bottleneck to a second container, and
- the analyte attached to the magnetic particles is moved, by means of a magnetic system, from the first container to the second container via the bottleneck, the second container being filled with all or part of the solution A and/or with another solution.

It should be noted that it is also possible for the preparation of the sample in which the analyte is attached to the magnetic particles to be carried out directly in the first container. This is also valid for the methods of concentration set out below.

For the purposes of the present invention, the expression "transporting the analyte" is intended to mean moving the analyte from one container to another container, with or without the liquid medium in which the analyte is present. The usefulness of such a transport, obtained by virtue of the method and of the device of the present invention, and also the applications and advantages which ensue therefrom, will become clearly apparent to those skilled in the art on reading the present description.

The present invention also provides a method of concentrating an analyte present in a sample, in which:

- a solution A in which the analyte is attached to magnetic particles is prepared from the sample,
- the solution A is introduced into a first container of volume $\alpha$ connected via a bottleneck to a second container of volume $\beta$, the volume $\beta$ being smaller than the volume $\alpha$, and
- the analyte attached to the magnetic particles is moved, by means of a magnetic system, from the first container to the second container via the bottleneck, the second container being filled with the solution A and/or with another solution.

The analytes are defined above.

The preparation of the solution A from the sample comprises a step in which the analyte is attached, preferably reversibly, to magnetic particles. The usefulness of this reversibility is explained below.

The magnetic particles are of a size which is suitable in particular for the analyte to be isolated, and for the volume of solution A. They may be submicrometer in size, for example when the analyte is a molecule.

The amount of particles used depends in particular on the nature and on the amount of analyte to be attached; the number of particles is preferably sufficient to attach all of the analyte. The magnetic particles which can be used in the method of the present invention can be, for example, products such as those having the trade mark Dynabeads from the company Dynal (Norway) or MACS from the company Miltenyi Biotec (Germany), or else products from the company Immunicon Corp. (USA).

In general, the magnetic particles which can be used are conventionally used in molecular or cell biology. They should in particular be superparamagnetic in order to rediffuse spontaneously after the magnetic field has been switched off.

Examples of protocols for attaching or for capturing the analyte on the magnetic particles can be found, for example, in the references *Bioscience Product Catalogue* 2000, and *Miltenyi Biotec, Tri Magnétique de Cellules, Séparation de biomolécules [Magnetic Cell Sorting, Separation of biomolecules]* 1999. The main particles available are the particles from Dynal, Seradyn, BioMag, Spherotec or Estapor (trade marks). Such particles can be coated with capture oligonucleotides, by adsorption or covalence. Documents U.S. Pat. Nos. 4,672,040 and 5,750,338 describe methods which can be used for the present invention. A particularly advantageous embodiment of these magnetic particles is described in the patent applications filed by one of the applicants under the following references:

PCT/FR 97/00912 under French priority of 24 May 1996, and

PCT/FR 99/00011 under French priority of 6 Jan. 1998.

In the latter of these patent applications, it involves thermosensitive magnetic particles each having a magnetic core covered with an intermediate layer. The intermediate layer is, itself, covered with an outer layer based on a polymer capable of interacting with at least one biological molecule; the outer polymer is thermosensitive and has a predetermined lower critical solubility temperature (LCST) of between 10 and 100° C., and preferably between 20 and 60° C. This outer layer is synthesized from cationic monomers, which generate a polymer having the ability to bind nucleic acids. This intermediate layer isolates the magnetic charges from the core, in order to avoid problems of inhibition of techniques for amplifying these nucleic acids.

According to the invention, the analyte reversibly attached to the magnetic particles can be released from said particles in the second container. Specifically, it may be necessary to release the analyte so that it may have easier access to, or be more readily accessible to, chemical reagents and/or the means used to demonstrate it.

According to the invention, the magnetic particles released from the analyte can be moved out of the second container by means of a magnetic system. This may be useful, for example, for avoiding any prejudicial interaction of the particles with the released analytes and/or with chemical reagents and/or means used to demonstrate it.

According to the invention, the release of the analyte being sought, or elution of the analyte, can be carried out for example in a buffer solution, for example by heating or another suitable method. The methods of release which can be used are all conventional methods of the state of the art. Chromatographic techniques offer an entire panoply of techniques for releasing proteins or another ligand, which can be used in the method of the present invention, such as a change in pH or a change in ionic strength, or a change of solvent, or else transferring into buffer containing EDTA or any other metal cation-chelating substance if the analyte is attached to the particle by a metal-chelate technique. If the analyte is an oligonucleotide, heating may for example be carried out at a temperature of 50 to 60° C. for an oligonucleotide 15 to 25 bases long, in order to dissociate all the analytes from the magnetic particles.

According to the invention, the magnetic system is a system which makes it possible to create a fixed or variable magnetic field engendering the application of a force on the magnetic beads, capable of immobilizing them or of moving them. It may consist of a set of magnets or coils.

It may also be an integrated coil, produced for example by microtechnological methods such as deposition of photosensitive masking materials and resins, insolation of these resins and etching of motifs on a micron scale, for example. Coils of this type are, for example, manufactured collectively using the abovementioned technology to produce reading/writing heads for hard disks.

According to the invention, after having been transported, the magnetic particles can be resuspended, for example in the second container, by switching off the magnetic field created by the magnetic system.

According to a variant of the present invention, the inventors also provide a method of concentrating an analyte present in a sample, in which:

a solution A in which the analyte is attached to magnetic particles is prepared from the sample, the solution A is introduced into a first container of volume $\alpha$ connected via a bottleneck to a second container of volume $\beta$, the volume $\beta$ being smaller than the volume $\alpha$, the analyte attached to the magnetic particles is moved, by means of a magnetic system, from the first container to the bottleneck, the analyte attached to the magnetic particles is released from said particles in the bottleneck, the analyte is transported, by movement of a liquid, from the bottleneck to the second container.

According to a variant of the method of concentration of the present invention, the analyte can be released in the second container, and the analyte can be moved either by transport of the liquid containing the analytes, or with transport by movement of a liquid from the second container to a third container.

According to the invention, the magnetic particles released from the analyte can be moved from the second container to the first container via the bottleneck, or from the bottleneck to said first container, by means of a magnetic system.

According to the invention, as described above, the analyte can be released from the magnetic particles by modification of the physical or chemical conditions, for example by heating or by reaction with at least one substance present in the other solution.

According to the invention, an agent for immobilizing the analyte can be attached to all or part of at least one wall of the second container or of any solid support present in said second container. Such supports can, for example, consist of silica beads, solid, hollow or porous glass beads, quartz particles, grains of sand, grains of vermiculite, zeolite and/or feldspar, glass wool and/or rock wool, clay beads, cork particles, polystyrene beads, polyethylene beads, polypropylene beads, aggregated beads of polyethylene of small size, of varying porosity and thickness, latex beads, gelatine-coated beads, and resin grains.

According to the invention, the bottleneck may be in the form of a capillary. This form may be advantageous, for example, for limiting the diffusion of the analyte from the second container to the first container when said analyte has been released from the magnetic particles.

The present invention also provides a method of demonstrating an analyte in a sample, in which:

the analyte is concentrated by means of a method of concentration of the present invention;

the analyte is demonstrated in the second container or in any other container connected directly or indirectly to the second container.

The second container or reaction chamber or any other container connected directly or indirectly to the second container can contain one or more reagent(s) which is (are) dry or in solution, intended to react directly or indirectly with the analyte. The term "indirectly" is intended to mean that several successive chemical reactions may be carried out on the analyte or one of its derivatives obtained. Magnetic particles in the form of tablets are described in the state of the art, for example in document EP-A-0 811 694. The production of tablets is also well described in the state of the art, for example in documents U.S. Pat. Nos. 4,678,812 and 5,275,016. This production mentioned above can be used to synthesize the other tablets which will be subsequently set out, such as:

a tablet which comprises structural constituents, such as dNTPs, primers or ions, for subsequent amplification as described in patent U.S. Pat. No. 5,098,893 or the article "Ambient-temperature-stable molecular biology reagents" R. Ramanujam et al., Product Application Focus, Vol. 14, No. 3 (1993), 470-473, for example, a tablet containing functional constituents, such as enzymes which, combined with the structural constituents mentioned above, make it possible to carry out an amplification. Examples of such tablets are given in patent U.S. Pat. No. 4,891,391, patent applications WO-A-87/00196 and WO-A-95/33488 or the article "Extraordinary stability of enzymes dried in trehalose: simplified molecular biology", by C. Colaco et al., Bio/Technology, Vol. 10, September 1992, 1007-1011.

According to the present invention, it is possible, for example, to envisage hybridization plots attached to a surface of the second container such that they are accessible to the analyte when it is in the second container. This can be produced, for example, in the form of an integrated DNA chip. Thus, according to the present invention, when the analyte to be demonstrated is a nucleic acid, it can be demonstrated using nucleic acid chip technology.

According to the present invention, the second container can therefore be a reservoir of a microcomponent, for example a biochip, for example a DNA chip. The term "biochip" is intended to mean any solid support to which ligands are attached and, in particular, the term "DNA chip" is intended to mean any solid support to which nucleic acids are attached. The method of attaching the ligands can be carried out in various ways, and in particular by adsorption or covalence, such as, for example, in situ synthesis by photolithographic techniques or by a piezoelectric system, or by capillary deposition of preformed ligands. By way of illustration, examples of these biochips applied to DNA chips are given in the publications by G. Ramsay, Nature Biotechnology, 16, p. 40-44, 1998; F. Ginot, Human Mutation, 10, p. 1-10, 1997; J. Cheng et al., Molecular diagnosis, 1(3), p. 183-200, 1996; T. Livache et al., Nucleic Acids Research, 22(15), p. 2915-2921, 1994; J. Cheng et al., Nature Biotechnology, 16, p. 541-546, 1998 or in patents U.S. Pat. No. 4,981,783 (Augenlicht), U.S. Pat. No. 5,700,637 (Southern), U.S. Pat. No. 5,445,934 (Fodor), U.S. Pat. No. 5,744,305 (Foder), U.S. Pat. No. 5,807,522 (Brown).

According to the invention, the second container can also be an entry chamber to another container for another method. Thus, the second container can be connected directly or indirectly to another container used for other chemical reactions or steps of a method targeting the analyte or one of its derivatives, such as a purification, an amplification, a labelling, etc. For example, the other container or chamber can be a PCR chamber for amplifying a gene, optionally then with analysis in a "lab-on-a-chip" ("micro-total analysis system": Micro-Tas).

However, all the amplification techniques can be used. Thus, for the amplification of the nucleic acids, the following techniques, inter alia, exist:

PCR (Polymerase Chain Reaction), as described in patents U.S. Pat. Nos. 4,683,195, 4,683,202 and 4,800,159, LCR (Ligase Chain Reaction), set out, for example, in patent application EP-A-0 201 184, RCR (Repair Chain Reaction), described in patent application WO-A-90/01069, 3SR (Self Sustained Sequence Replication) with patent application WO-A-90/06995, NASBA (Nucleic Acid Sequence-Based Amplification) with patent application WO-A-91/02818, SPSR (Single Primer Sequence Replication) with patent U.S. Pat. No. 5,194,370, and TMA (Transcription Mediated Amplification) with patent U.S. Pat. No. 5,399,491.

According to the invention, other reagents can be used, such as lyophilized reagents, for example to carry out a homogeneous test to detect the analyte, for example by fluorescence transfer.

According to the invention, in a nonlimiting manner, the analyte is defined above.

The present invention also provides a device for transporting an analyte attached to magnetic particles, present in a liquid, said device comprising:

a first container intended to contain a liquid and connected via a bottleneck to a second container, a magnetic system for moving the magnetic particles to which the analyte is attached, from the first container to the second container via the bottleneck.

According to the invention, the volumes of the first and second containers are preferably suitable for the volumes of solutions to be handled. These volumes may be less than or equal to 10 ml.

The present invention also provides a device for concentrating an analyte attached to magnetic particles, present in a liquid, said device comprising:

a first container of volume $\alpha$ intended to contain a liquid, connected via a bottleneck to a second container, said second container of volume $\beta$ smaller than the volume $\alpha$ of the first container, and a magnetic system for moving the magnetic particles to which the analyte is attached, from the first container to the second container via the bottleneck.

Some elements of these devices have already been described for the method of the present invention, and should be taken into consideration with the description below.

According to the present invention, these containers can be used, for example, as reaction chambers. The abovementioned techniques also make it possible to produce capillaries with a cross section of a few square microns to a few hundred thousand square microns for the transfer of solutions, or of an analyte attached to microparticles, according to the present invention, from a first container to a second container, for example from a reaction chamber to another reaction chamber.

According to the invention, the $\alpha/\beta$ volume ratio can, for example, be from 10 to 1000.

According to the invention, the first container can, for example, have a volume of approximately 0.1 to 100 μl.

According to the invention, the second container can have a volume of approximately 0.01 to 1 μl.

The invention therefore allows a reduction in volume which is 100 to 1000 times greater than that which could be achieved with laboratory practices or automated "macroscopic" systems of the prior art handling liquids with pipettes and flasks of a few tens of microliters. As a result, it makes it possible to concentrate a sample by the same factor 100 to 1000.

In fact, techniques for photolithographic etching of solid substrates, for example of silicon, of silica or of glass, or for high-precision moulding of plastic materials, make it possible to produce containers of submillimeter sizes, or even of the order of a few microns in at least one direction, which can therefore have volumes reduced to fractions of a microliter.

According to the invention, the first container and/or the second container can have a form which converges towards said bottleneck. The bottleneck can, for example, be in the form of a capillary as described in the preceding paragraph.

According to the invention, the bottleneck can, for example, have a cross section between 1 $\mu m^2$ and 1 $mm^2$, preferably 100 $\mu m^2$ and 0.1 $mm^2$.

According to the invention, the second container and/or the bottleneck can be equipped with fluid inlet/outlet channels. These channels of course have a cross section which is adjusted as a function of the volumes of solution they are intended to contain. Thus, for example, for demonstration of the analyte, when it is a nucleic acid, in the second container by hybridization on capture probes carried by a solid support, these channels can be used to perform the washing necessary before the reading step.

According to the invention, the abovementioned devices can comprise a duct in the form of a capillary present in the second container and directly connecting said container to the outside. During operations consisting of filling and/or transferring fluid into the second container, this duct serves to evacuate the fluid initially present in the container, whether this is air or liquid. The presence of air in the second container is only one possibility. There may be ducts at other sites, for example at the bottleneck, in the first container, etc. These venting ducts can be controlled, for example, with ball valves.

The invention may therefore, by using microtechnological techniques, be integrated into the devices today called "lab-on-a-chip" or alternatively "micro-Total-Analysis-System" (MicroTAS).

In the "lab-on-a-chip" example, the device of the present invention can be combined with other functions in order to form a more complete and more precise system of biological analysis.

For example, the device of the present invention can be the first element of a set comprising:

1. a concentrating/volume reducing module,
2. an amplifying module,
3. a separating module, for example for separating by electrophoresis.
4. a detecting module.

An example of an integrated device comprising elements 2, 3 and 4 above is described in the reference M. A. Burns et al., *An Integrated Nanoliter DNA Analysis Device,* Science, Vol. 282, Oct. 16, 1998.

In certain implementations of the present invention, the concepts of reaction chamber and transfer channels can therefore merge since these "labs-on-a-chip" make it possible to carry out continuous methods for which the reactions take place in capillaries, for example in certain techniques of capillary electrophoresis and of PCR.

The invention may, for example, be useful when the analyte being sought is initially present in a sample of large volume, but in limited amount.

The invention provided makes it possible, for example using the abovementioned microtechnologies, to concentrate a solution of molecules the detection of which is desired, or to move an analyte from a first solution to a second solution in a volume of less than a microliter, which is completely inaccessible using conventional laboratory methods.

The present invention can be implemented, for example, in an automated in vitro diagnostic system, or a system for detecting biological contaminants, in fields such as agrofoods and/or industrial microbiological control.

The invention can be used, for example, for the ultrasensitive detection without amplification of pathogens in a biological sample. The nucleic acids of the pathogens potentially present in a sample can be extracted by usual techniques. They can then be purified and concentrated, still by standard techniques, to a buffer volume of a few tens of microliters.

The use of the device of the present invention or microcomponent makes it possible, in this case, to concentrate the biological material in the volume of the reaction chamber which corresponds to the second component. Here, subsequent steps of hybridization on a flat support and of detection make it possible to detect the presence or absence of nucleic acids of a given sequence, characteristic of the infection of the sample.

The use of the invention therefore makes it possible to very greatly increase the sensitivity of a test, given equal performance of the detection system.

The present invention can, for example, be used to improve immunoassays. Specifically, for immunoassays in which there is a problem of sensitivity, the use of the invention, as described above, by concentrating the biological material in a very small volume, makes it possible to greatly increase their sensitivity.

For immunoassays in which the amount of biological material to be detected is sufficient, the use of the invention makes it possible to concentrate the specimen, and therefore to decrease the duration of the immunoreaction.

Other characteristics and advantages will also become apparent in the examples below, given of course by way of nonlimiting illustration, with reference to the attached figures.

BRIEF DESCRIPTION OF THE FIGURES

In these figures, the identical references indicate identical elements.

EXAMPLES

Example 1

Example of Preparation of the Solution A

The biological sample is treated by conventional molecular biology means in order to obtain a solution containing the target RNA molecules to be detected; this solution has a volume of 200 microliters and the buffer solution is as follows: 10 mM Tris, 1 mM EDTA, 1M NaCl, 0.05% triton X-100, 0.14 mg/ml salmon DNA.

Added to this solution are 2 μl of a solution of capture oligonucleotides; this solution of capture oligonucleotides consists of: 10 mM Tris, 1 mM EDTA, pH 8, $10^{11}$/μl capture oligonucleotide; the capture oligonucleotide is a 5'-biotinylated oligonucleotide with a sequence of, for example, 32 bases, complementary to a subsequence of the target DNA.

The mixture is incubated for 2 h at 35° C.

1 μl of undiluted Immunicon Corporation ferrofluid streptavidin particles is introduced.

Incubation is carried out for 30 minutes at 35° C.

Under these conditions, more than 95% of the target molecules are immobilized on the magnetic particles.

Example 2

Device According to a First Embodiment of the Present Invention

The device or component described in this example is a microcomponent which makes it possible to reduce 100- to 1000-fold the volume of buffer in which an analyte being sought is located, while at the same time conserving the amount of analyte present in the initial sample.

Figure 1:
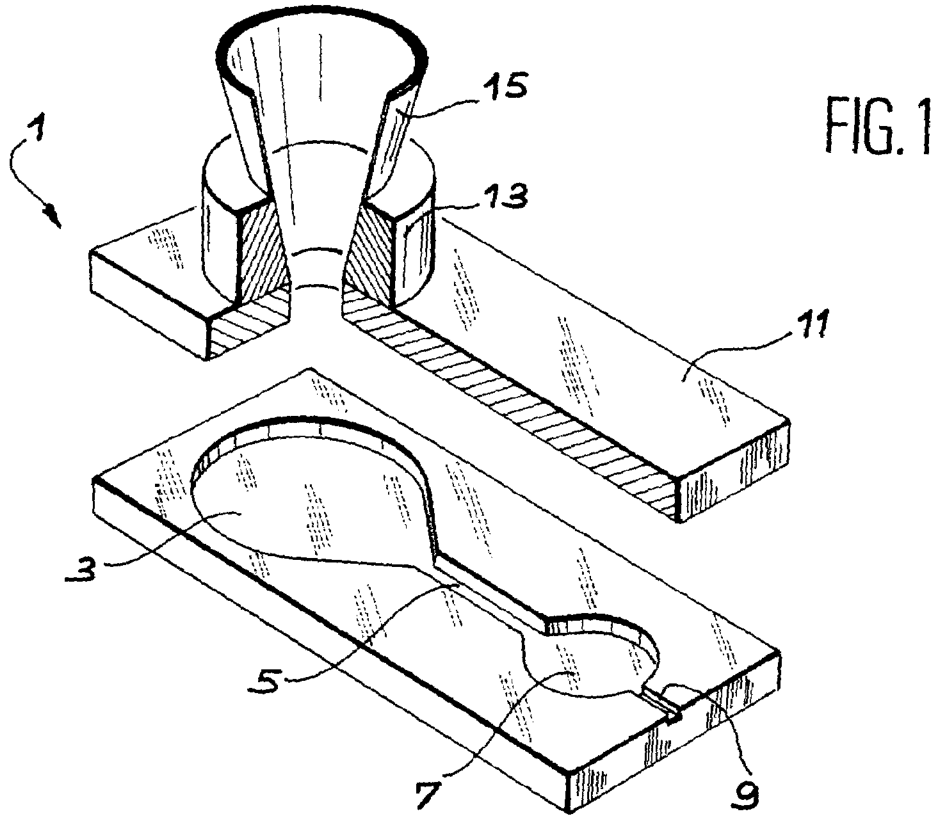
FIG. 1 is a diagrammatic exploded perspective representation with a partial section of a first embodiment of a device according to the present invention.

The general architecture of component 1 is represented in FIG. 1. It consists of an introduction chamber 3, optionally extended by an introduction device consisting of parts 13 and 15, connected to a reaction chamber 7 via a bottleneck 5, here represented in the form of a capillary. The particular forms of the two chambers are given by way of example. The chambers and the capillary can be different in form or size depending on the application or the technology for producing the component. FIG. 1 suggests a method of production according to which the component is produced by etching the chambers and the bottleneck into a flat material, and then assembling the cover 11 by adhesive bonding or any other method of attachment. It is one possible method of production, but the invention does not depend on this method of production. Any other technology, in particular:

- making it possible to hollow out a material directly to produce cavities in the shape of the chambers and the bottleneck,
- or which consist in hollowing out the chambers 3 and 7 and also the bottleneck in the upper plate, in the example in the cover 11, instead of hollowing them out in the lower plate, may be used to produce the device.

Mention may, for example, be made of techniques like "LIGA" using lithography, electroplating and moulding.

A duct 9 allows evacuation of the air or liquid fluids when the chambers are filled or liquids are transferred into them.

The sample and the various reagents or buffers can be introduced into the devices in various ways. Two of them are given here by way of examples.

This first embodiment, illustrated in FIG. 1, is implemented by making an orifice in the cover 11 of the device and equipping this orifice with a conical cuvette 15. A cylindrical part 13 is used to maintain the conical cuvette in position and to ensure leaktightness between the conical cuvette and the device. By applying, for example, a pipette, or the nozzle of a diluter or of a syringe to the conical cuvette, it is possible to "push" the buffer or a reagent into the device by exerting a pressure on the liquid. The air or any other liquid or gaseous fluid initially present in the device will be evacuated from the device via the duct 9. This duct here opens into the reaction chamber, but it may be placed, as appropriate, at other places on the device. It is even possible to optionally have several ducts.

Figure 2:
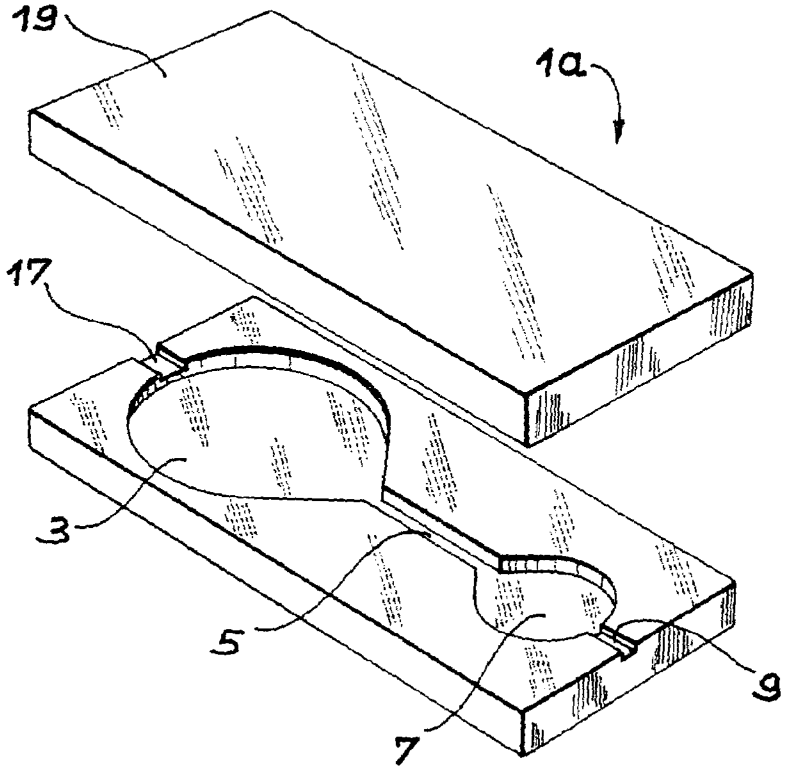
FIG. 2 is a diagrammatic exploded perspective representation of a second embodiment of a device according to the present invention.

A second embodiment for introducing liquid into the device is represented in FIG. 2. In this embodiment 1(a), the liquids are introduced via a capillary 17, itself connected to the outside of the device by an interface, not represented in the figure. The cover 19 does not have an orifice.

Example 3

Concentration with Transport on Magnetic Particles

The method described in this example makes it possible to reduce 100- to 1000-fold the volume of buffer in which an analyte being sought is located, while at the same time conserving the amount of analyte present in the initial sample. It uses the device represented in the preceding example.

The component is prefilled with buffer without analyte being sought and without magnetic particles. This buffer can be introduced by pouring the required amount into the conical cuvette 15 represented in FIG. 1, and applying a pneumatic pressure to this conical cuvette. Once the component has been filled, the excess buffer present in the conical cuvette 15 is removed, for example using a pipette.

The sample, composed of a certain amount of buffer, for example of the order of 30 μl, in which the analytes being sought have been attached to magnetic particles beforehand, is placed in the conical cuvette 15.

Figure 4:
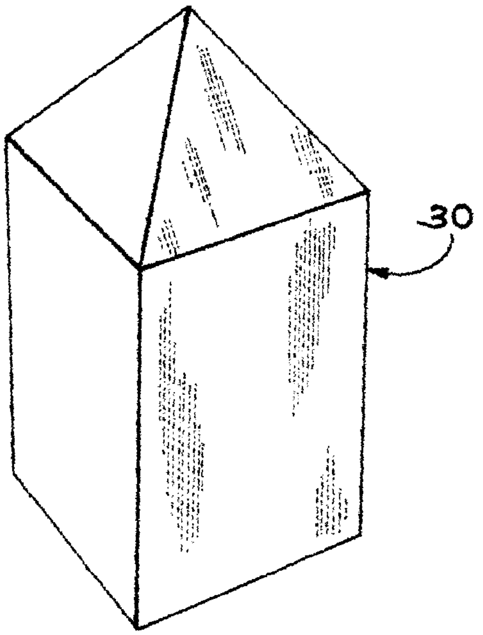
FIG. 4 is a diagrammatic representation of a first magnet which can be used for implementing the present invention.

The magnetic particles are then attracted towards the bottom of the introduction chamber 3 (FIG. 1) using a magnet, for example the magnet 30 in the shape indicated in FIG. 4, positioned under the device, at the base of the conical cuvette. The magnetic particles are then brought together into a pellet which is small in size.

Figure 5:
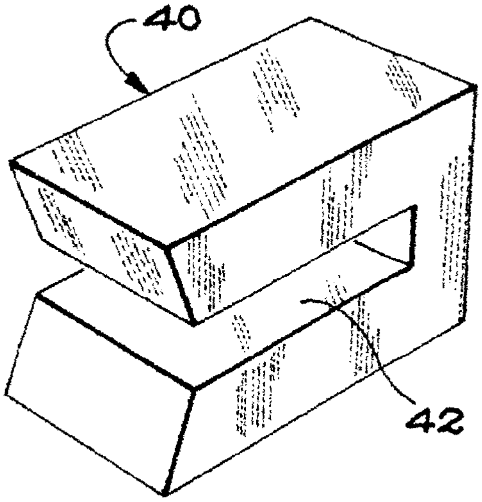
FIG. 5 is a diagrammatic representation of a second magnet which can be used for implementing the present invention.

Using another magnet, for example the magnet 40 in the shape indicated in FIG. 5, arranged such that the device is located in its gap 42, the pellet is attracted and transported from its initial position in the first introduction chamber 3, through the capillary 5, into the reaction chamber 7.

The analyte is then released from the magnetic particles by heating (elution) inside the reaction chamber 7. During this operation, the magnetic particles are optionally resuspended in the reaction chamber 7 by withdrawing the magnet.

The magnetic particles are again brought together into a pellet in the reaction chamber 7, again using a magnet, for example in the shape presented in FIG. 4. They are then again transported through the capillary 5, but in the opposite direction to previously, from the reaction chamber 7 to the introduction chamber 3, using a magnet, for example in the shape presented in FIG. 5.

The final result of this series of operations is the transport of all of the analytes from the conical cuvette 15 to the reaction chamber 7, with a much smaller volume.

Example 4

Concentration with Fluid Transport

The method described in this example is a variant of the preceding method.

As previously, the component is prefilled with buffer without magnetic particles. The sample, composed of a certain amount of buffer, for example of the order of 30 μl, in which the analytes being sought have been attached to magnetic particles beforehand, is placed in the conical cuvette 15. The magnetic particles are attracted towards the bottom of the introduction chamber 3 (FIG. 1) using a magnet, for example in the shape indicated in FIG. 4. The magnetic particles are then brought together into a pellet which is small in size.

Using another magnet, for example in the shape indicated in FIG. 5, arranged such that the device is located in its gap, the pellet is attracted and transported from its initial position into the capillary 5 (and no longer into the reaction chamber 7).

The analyte is released from the magnetic particles by heating (elution) inside the capillary 5. During this operation, the magnetic particles are optionally resuspended in the capillary by withdrawing the magnet.

The magnetic particles are again brought together into a pellet in the capillary, again using a magnet, for example in the shape presented in FIG. 4. At this time, the analytes are free in solution inside the capillary. By pushing buffer into the device by overpressure at the conical cuvette 15, movement of liquid in the capillary towards the reaction chamber 7 is brought about. The analytes in solution are thus entrained by the movement of the liquid into the reaction chamber 7. The magnetic particles, themselves, remain in position in the capillary, maintained in position in the form of a pellet by the fixed magnet.

The final result of this series of operations is, as previously, the transport of all the analytes from the conical cuvette 15 to the reaction chamber 7, with a much smaller volume.

According to a variant of this method, the magnetic particles are in the form of dry entities already present in the introduction chamber 3. Such entities are well described in patents U.S. Pat. Nos. 5,750,338 and 4,672,040. Introduction of the sample, into said chamber 3, solubilizes the magnetic particles, which then attach to the analyte present from the beginning in said sample.

Example 5

Use of the Invention for Demonstrating the Analyte in a Homogeneous Detection Assay In this example, the analyte is demonstrated by using the "Molecular Beacons" technique, as described in S. Tyagi and F. R. Kramer, Nat. Biotechnol. 14: 30-308, 1996.

Briefly, this technique consists in placing the target molecules with nucleic acid probes, the "Molecular Beacons", which have the following structure: the probe sequence, which is complementary to the target, is extended on both sides by two arms a few nucleotides long, complementary to one another. A fluorophore, for example the EDANS group, is attached to one of the arms, whereas a fluorescence inhibitor, for example the DABCYL group, is attached to the other arm. In the absence of target, the two arms of the probe hybridize to one another and the EDANS fluorescence is extinguished by the DABCYL. When the probe hybridizes to the target, the two groups are at a distance from one another, and the EDANS fluorescence is released. Thus, the presence, and even the concentration, of the analyte is revealed by the fluorescent signal and the strength of this signal.

The implementation of this technique in a device in accordance with the invention is, for example, as follows:

1. preparation of the solution A to be analysed, the analyte being a nucleic acid,
2. filling of the second container 7 of the device, and also of the bottleneck 5 and of the bottom 3 of the first container, with a revealing solution containing the nucleic acid probes previously defined, required to detect the analyte,
3. introduction of the solution A into the first container 3 extended by the cone 15,
4. magnetic concentration of the magnetic particles at the bottom of the first container 3, then magnetic transport of the magnetic particles into the second container 7, for example according to the procedures described in Example 3,
5. heating of the entire device at 60° C., holding at this temperature for 1 to 2 minutes. The analyte is then released from the particles,
6. magnetic transport of the magnetic particles from the second container 7 to the first container,
7. return to the appropriate temperature for the hybridization of the beacon nucleic acid probe, for example 25° C.,
8. reading of the fluorescence in the second container 7, for example by placing the device under an epifluorescence microscope equipped with a photomultiplier.

The advantage of this procedure compared to the state of the art is to concentrate the analyte in an alpha/beta ratio, for example 100-fold, and therefore to relatively decrease the residual fluorescence of the "Molecular Beacon" probes, and thus to increase accordingly the signal to noise ratio intrinsic to this technique for demonstrating an analyte. The sensitivity of the assay is therefore increased accordingly.

Example 6

Use of the Invention to Demonstrate the Analyte Using a DNA Chip

In this example, the analyte is demonstrated by hybridization on a DNA chip; the DNA chip has the advantage, compared to the labelling technique presented in Example 5, of being able to perform many hybridizations in parallel, and therefore of offering the biologist a much greater analytic capacity.

In this example, the bottom of the second container 7 is a DNA chip, consisting, for example, of about twenty hybridization plots. The chip is produced by depositing DNA according to standard means of the DNA chip prior art.

Figure 3:
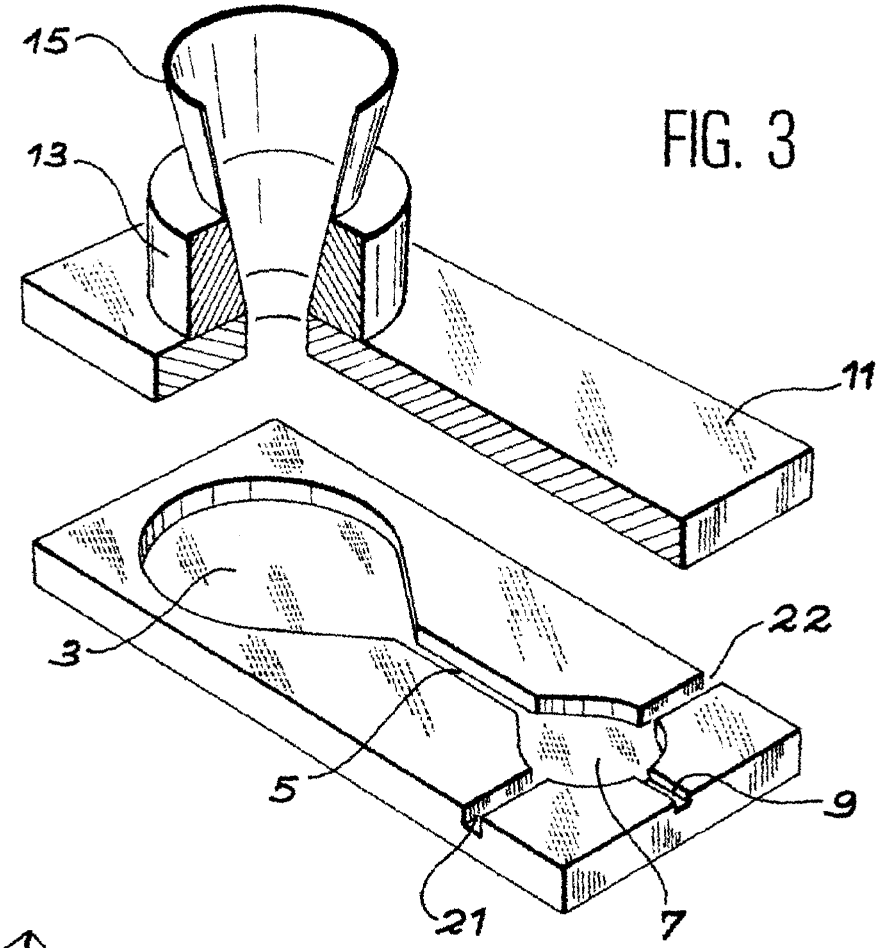
FIG. 3 is a diagrammatic exploded perspective representation with a partial section of a third embodiment of a device according to the present invention.

The implementation of this technique in a device in accordance with the invention may, for example, be as follows:

1. preparation of the solution A to be analysed, the analyte being a nucleic acid, labelled with a fluorescent group, for example fluorescein, by conventional means of the prior art,
2. filling of the second container 7 of the device, and also of the bottleneck 5 and of the bottom 3 of the first container, with the hybridization buffer, for example: 10 mM Tris, pH 8, 1 mM EDTA, 1M NaCl, 0.05% triton X-100, 0.14 mg/ml salmon DNA,
3. introduction of the solution A in the first container 15,
4. magnetic concentration of the magnetic particles at the bottom 3 of the first container, then magnetic transport of the magnetic particles into the second container 7, for example according to the procedures described in Example 3,
5. heating of the entire device at 60° C. The analyte is then released from the particles,
6. magnetic transport of the magnetic particles from the second container 7 to the first container 3,
7. hybridization under the temperature and time conditions suitable for the DNA chip under consideration. For example, hybridization for 30 minutes at 40° C.,
8. washing by passing a washing solution, for example 10 mM Tris, 1 mM EDTA, 1M NaCl, 0.5% triton X-100, into the second container 7, by means of the fluid inlet and outlet via the openings 21, 22 represented in FIG. 3,
9. reading of the fluorescence present on the DNA chip, for example by placing the device under an epifluorescence microscope equipped with a CCD camera, and using a suitable magnification.

As in the preceding example, the concentrating of the analyte before hybridization thereof on the DNA chip allows a more rapid reaction of the analyte on the DNA chip. This acceleration of the kinetics compared to the state of the art makes it possible either to decrease the hybridization time or to increase the sensitivity of detection of the system, since this sensitivity is, in general, limited by the kinetics of hybridization of the analyte on the DNA chip.

Example 7

Use of the Invention as a Point of Entry for a μTAS

In this example, the invention is used as a point of entry to a μTAS more complex than a device composed only of two containers separated by a bottleneck. Taken as an example of a μTAS is that presented by the team of A. Northrup, which consists of an amplification chamber, followed by capillary electrophoresis of the amplified products and detection (see Anal. Chem. 1996, 68, 4081-4086).

In this example, the second container is in fact a PCR amplification chamber, for example produced by microtechnological means. This means that the second container is equipped with a heating means, a cooling means and a temperature sensor, which makes it possible to apply thermal cycles to the liquid sample contained in the second container 7. The fluid inlet-outlet 21, 22 crossing this second container is the channel for injection by electrophoresis of the amplified sample into the separating capillary. The separating capillary is not shown in our figures (see FIG. 1 of the abovementioned article), nor are the microreservoirs for applying the electric fields required for the injection and then for the separation by electrophoresis.

The second container also contains dry pellets containing all the products required for the PCR amplification; these products are "glassified" by well-known techniques, and the glassified pellets, in bead form, containing the various products required for the amplification, are placed in the second container before the cover is put into position. The production of these pellets is well described in the state of the art, for example U.S. Pat. Nos. 4,678,812 and 5,275,016.

The separating capillary also contains a separating gel, for example made of hydroxyethylcellulose, which itself contains a fluorescent DNA marker, for example thiazole orange. Thus, the DNA fragments will be labelled with the thiazole orange as they migrate electrophoretically in the separating capillary.

The use of such a device is, for example, as follows:

1. preparation of the solution A to be analysed, the analyte being a nucleic acid,
2. filling of the entire device, in particular of the capillaries, with the electrophoresis solution; the reagent pellets present in the second container begin to hydrate,
3. introduction of the solution A into the first container 15,
4. magnetic concentration of the magnetic particles at the bottom of the first container 3, then magnetic transport into the second container 7, according to the procedures of Example 3 above,
5. heating of the second container 7 at 60° C. Holding for 10 to 30 minutes depending on the reagent pellet to be dissolved. Specifically, the main aim of this heating is to accelerate the redissolving of the reagent pellets present in the container,
6. thermal cycling to perform the target amplification operation (magnetic particles exist which do not hinder the amplification, it is not therefore necessary to withdraw them from the amplification chamber),
7. injection by electrophoresis of the amplified sample into the outlet capillary,
8. capillary electrophoresis in the separating capillary, for example according to the procedures described in the abovementioned article,
9. detection of the amplified fragments, for example using an epifluorescence microscope equipped with a photomultiplier, the field of the microscope being located at the end of the separating capillary.

In this example, coupling the invention to an integrated system of amplification and capillary electrophoresis makes it possible:

- to concentrate the sample before amplification, for example 100-fold, and therefore to decrease the number of amplification cycles required (less than 8 cycles approximately), which limits the risks intrinsic to amplification (amplification bias according to the sequences, risk of cross-contamination, etc.),
- to decrease the volume of the sample for the amplification, and therefore to decrease the amounts of reagents required for the amplification, hence a saving in cost in terms of the reagents,
- to increase the number of samples which it is possible to process in parallel in the same device by virtue of the decrease in the size of the amplification chamber.

Moreover, the rapidity with which the entire chain is carried out, of the order of a few minutes for the magnetic transport, of 10 to 15 minutes for the amplification and of 1 to 2 minutes for the capillary electrophoresis, makes it possible to obtain results of excellent quality without it being necessary to isolate the compartments by means of valves.

The invention claimed is:

1. A method of concentrating an analyte present in a sample, comprising the following steps:

providing a solution A in which the analyte is attached to magnetic particles, by contacting the magnetic particles with the sample, in a first container of volume α connected via a bottleneck to a second container of volume β, the volume β being smaller than the volume α, moving the analyte attached to the magnetic particles, by means of a magnetic system, from the first container to the bottleneck, releasing the analyte attached to the magnetic particles from said particles in the bottleneck, moving the magnetic particles released from the analyte from the bottleneck to said first container by means of a magnetic system, and transporting the analyte from the bottleneck to the second container by movement of the solution A.

2. The method as claimed in claim 1, in which the analyte is released from the magnetic particles by modification of the physical or chemical conditions.

3. The method as claimed in claim 1, in which an agent for immobilizing the analyte is attached to all or part of at least one wall of the second container or of any solid support present in said second container.

4. The method as claimed in claim 1, in which the bottleneck is in the form of a capillary.

5. The method as claimed in claim 1, wherein the first container, the bottleneck and the second container are hollowed-out cavities in a single piece of material.

6. A method of concentrating an analyte present in a sample, comprising the following steps:

providing a solution A in which the analyte is attached to magnetic particles, by contacting the magnetic particles with the sample, introducing the solution A into a first container of volume α connected via a bottleneck to a second container of volume β, the volume β being smaller than the volume α, moving the analyte attached to the magnetic particles, by means of a magnetic system, from the first container to the bottleneck, releasing the analyte attached to the magnetic particles from said particles in the bottleneck, moving the magnetic particles released from the analyte from the bottleneck to said first container by means of a magnetic system, and transporting the analyte from the bottleneck to the second container by movement of the solution A.

7. The method as claimed in claim 6, in which the analyte is released from the magnetic particles by modification of the physical or chemical conditions.

8. The method as claimed in claim 6, in which an agent for immobilizing the analyte is attached to all or part of at least one wall of the second container or of any solid support present in said second container.

9. The method as claimed in claim 6, in which the bottleneck is in the form of a capillary.

10. The method as claimed in claim 6, wherein the first container, the bottleneck and the second container are hollowed-out cavities in a single piece of material.

* * * * *